United States Patent [19]

Torii et al.

[11] 4,166,188

[45] Aug. 28, 1979

[54] 2-(2-PENTYNYL) CYCLOPENTANOL DERIVATIVES

[75] Inventors: Sigeru Torii; Hideo Tanaka; Yuichi Kobayashi, all of Okayama, Japan

[73] Assignee: Otsuka Kagaku Yakuhin Kabushiki Kaisha, Osaka, Japan

[21] Appl. No.: 913,690

[22] Filed: Jun. 8, 1978

[30] Foreign Application Priority Data

Aug. 12, 1977 [JP] Japan .................................. 52-97181

[51] Int. Cl.² .............................................. C07C 69/74
[52] U.S. Cl. .................................... 560/122; 560/126; 560/127
[58] Field of Search ......................... 560/122; 562/504

[56] References Cited

U.S. PATENT DOCUMENTS 3,941,828  3/1976  Buchi .................................. 560/122

OTHER PUBLICATIONS

Tanaka, H. et al., "Synthesis of Methyl dl-Jasmonate and Methyl dl-2-Epijasmonate." Journal of Organic Chemistry, vol. 40, (1975), pp. 462–465.
Joulain, Daniel "Les Syntheses du Jasmonate de Methyle et des Composes Apparentes." Parfums, Cosmetiques, Aromes, No. 12, Nov./Dec. 1976, pp. 53–60.

*Primary Examiner*—James O. Thomas, Jr.
*Assistant Examiner*—L. Hendriksen
*Attorney, Agent, or Firm*—Armstrong, Nikaido, Marmelstein & Kubovcik

[57] ABSTRACT

A 2-(2-pentynyl) cyclopentanol derivative represented by the formula

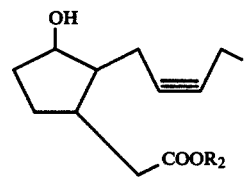

wherein $R_2$ is lower straight-chain or branched-chain alkyl, alkenyl or aralkyl, and process for preparing the same.

1 Claim, No Drawings

2-(2-PENTYNYL) CYCLOPENTANOL DERIVATIVES

This invention relates to novel 2-(2-pentynyl)cyclopentanol derivatives and a process for preparing the same.

The compounds of this invention are novel compounds represented by the formula

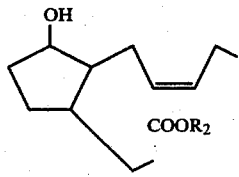

(1)

wherein $R_2$ is lower straight-chain or branched-chain alkyl, alkenyl or aralkyl.

The compounds of this invention are useful as intermediates for the synthesis of jasmonoid compounds which are important as perfumes.

The present compounds are produced by the following process:

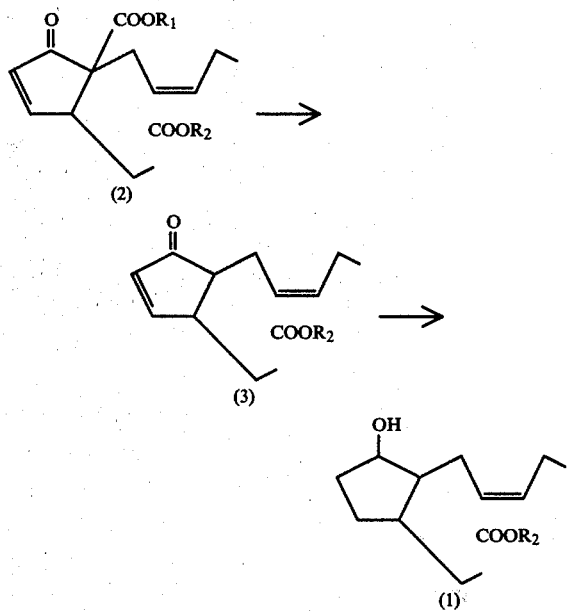

wherein $R_1$ and $R_2$ are each lower straight-chain or branched-chain alkyl, alkenyl or aralkyl.

The compound (2) which is used as the starting material of this invention is novel and prepared by the following process:

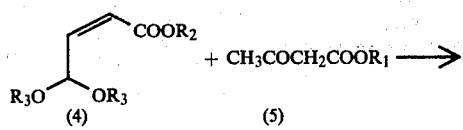

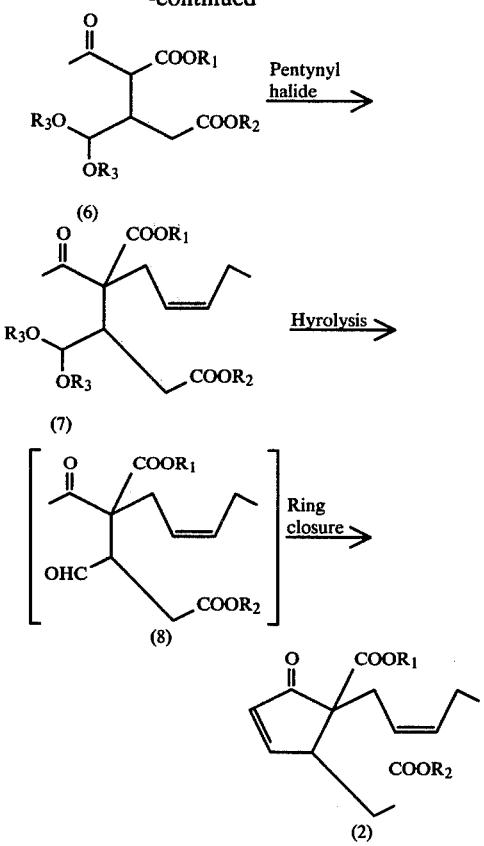

wherein $R_1$, $R_2$ and $R_3$ are as defined above.

The compound (4) is a cis-2-butenate derivative which is easily prepared for example by electrolytically oxidizing furfuryl alcohol. The compound (7) is obtained by subjecting the derivative and an acetoacetate (5) to condensation to prepare a compound (6) and reacting the compound (6) with pentynyl halide. The compound (7) gives a compound (2), the starting material of the invention, when subjected to ring closure directly or after hydrolysis.

The above-mentioned groups $R_1$, $R_2$ and $R_3$ are each lower straight-chain or branched-chain alkyl, alkenyl or aralkyl. Examples of groups $R_1$, $R_2$ and $R_3$ are alkyl groups such as methyl, ethyl, n-propyl, iso-propyl, n-butyl, sec-butyl, n-pentyl, neo-pentyl, n-hexyl, iso-hexyl, etc.; alkenyl groups such as vivyl, allyl, 1-propenyl, butenyl, pentenyl, hexenyl, etc.; and aralkyl groups such as benzyl, phenetyl, methylbenzyl, phenylpropyl, etc.

The decarboxylation of the compound (2) to the compound (3) proceeds with ease and without side reaction, whereby the carboxylate group in the 5th position of the compound (2) alone is selectively removed. This reaction is conducted advantageously in the presence of a solvent and a catalyst. Examples of useful solvents are inert solvents including aromatic hydrocarbons such as benzene and toluene; aliphatic ethers such as tetrahydrofuran, dioxane and ethyl ether; aliphatic hydrocarbons such as n-hexane and n-heptane; hydrocarbon halides such as dichloromethane and dichloroethane; and mixtures of such organic solvents. Examples of useful catalysts are sulfonic acids such as p-toluenesulfonic acid, benzenesulfonic acid; mineral acids such as hydrochloric acid and sulfuric acid; Lewis acids such as boron trifluoride, aluminum chloride and zinc chloride; organic acids such as formic acid and acetic acid. The reaction temperature is not particularly limited and is usually 30° to 120° C., preferably 60° to 100° C.

If the decarboxylation reaction is conducted with use of a solvent such as dimethylformamide or dimethyl sulfoxide and a catalytic amount of sodium chloride at a temperature of 100° to 200° C., preferably 130° to 180° C., the reaction gives the compound (3) and, at the same time, a compound of the formula

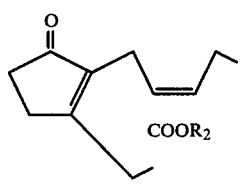

wherein $R_2$ is as defined above, as a by-product.

The selective reduction of the compound (3) to the compound (1) is conducted advantageously in the presence of a solvent and a reducing agent. Examples of useful solvents are aliphatic alcohols such as methanol, ethanol and isopropanol; and aliphatic ethers such as tetrahydrofuran, dioxane and ethyl ether. Examples of useful reducing agents are lithium aluminum hydride, lithium tri-tert-butoxyaluminum hydride, diisopropylaluminum hydride and like aluminum hydrides; and sodium borohydride, potassium borohydride and like borohydrides. The reducing agent is used preferably in an amount of about 0.1 to about 5 moles per mole of the compound (3). The reaction temperature, which is not particularly limited, is usually 10° to 70° C., preferably 30° to 50° C. Satisfactory results are obtained when the reaction is conducted usually for 1 to 3 hours.

The process described above yields the compounds (1) of this invention. The compounds (1) thus obtained can be easily isolated and purified in the usual manner as by extraction, washing, distillation, chromatography and recrystallization.

The present compounds (1) are useful as intermediates for the synthesis of jasmonoid compounds (J) which are important as perfumes. Compounds (J) can be produced from the present compounds by the process illustrated below.

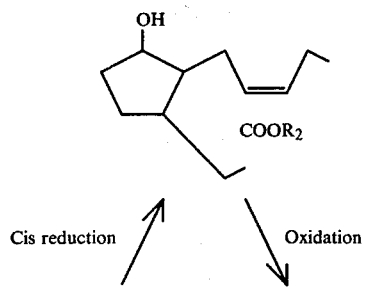

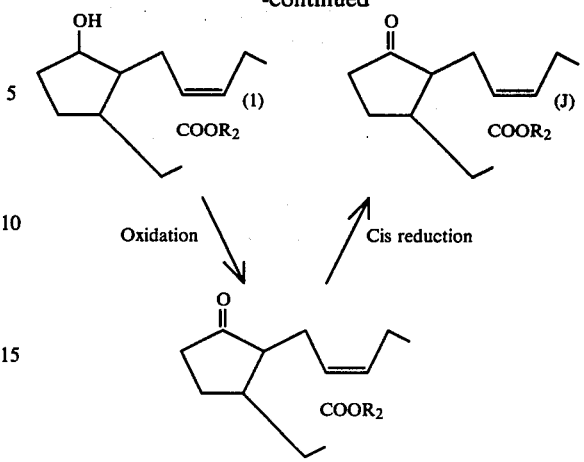

The term "cis reduction" as herein used means the reduction by which alkynyl is converted to cis-alkenyl.

This invention will be described below with reference to Examples and Reference Examples.

REFERENCE EXAMPLE 1

Into a 500-ml reactor are placed 40 g of potassium fluoride, 40 ml of dry tert-butanol, 123 g of methyl cis-4,4-dimethoxy-2-butenate and 36 g of tert-butyl acetoacetate. The mixture is heated at 100° C. with stirring on an oil bath for two days. On completion of the reaction, the tert-butanol is distilled off from the mixture. The residue is dissolved in ethyl acetate, and the solution washed with an aqueous solution of common salt and then dried. The solvent is removed from the product. The resulting residue is purified by a silica gel column and distilled at reduced pressure, giving methyl 4-tert-butoxycarbonyl-3-dimethoxymethyl-5-oxohexanoate (compound (6), $R_1=t$-Bu, $R_2=R_3=CH_3$) in a yield of 95.4%, b.p. 72°–76° C./0.014 mm Hg.

| Elementary analysis: | C | H |
|---|---|---|
| Found (%) | 56.65 | 8.13 |
| Calculated (%) | 56.59 | 8.23 |

IR: 2851 cm$^{-1}$ (CH$_3$O), 1736 cm$^{-1}$ (C=O), 1715 cm$^{-1}$ (C=O).

NMR (CCl$_4$): 1.43 (bs 9, CH$_3$), 3.19–3.38 (m 6, CH$_3$O), 3.58–3.72 (m 3, CH$_3$OCO), 3.19–3.72 (m 1, CH), 4.31 (t 1, 5 Hz, OCHO).

REFERENCE EXAMPLE 2

A 1.38 g quantity of potassium carbonate and 308 mg of potassium iodide are placed into a reactor. Acetone (30 ml) and a solution of 450 mg of methyl 4-tert-butoxycarbonyl-3-dimethoxymethyl-5-oxohexanoate in 10 ml of acetone are further placed into the reactor. Subsequently 270 mg of pentynyl bromide is added to the mixture. The resulting mixture is stirred at room temperature for one hour and thereafter refluxed at 70° C. for 13 hours. On completion of the reaction, the mixture is cooled to room temperature, and the solids are separated off. The product is concentrated in a vacuum, and the residue purified by a silica gel column, giving methyl 4-acetyl-4-tert-butoxycarbonyl-3-dimethoxymethyl-6-nonynoate (compound (7), $R_1=t$-Bu, $R_2=R_3=CH_3$) in a yield of 91%.

| Elementary analysis: | C | H |
| --- | --- | --- |
| Found (%) | 62.54 | 8.35 |
| Calculated (%) | 62.50 | 8.39 |

IR: 2837 cm$^{-1}$ (CH$_3$O), 1729 cm$^{-1}$ (>C=O), 1710 cm$^{-1}$ (>C=O), 1430 cm$^{-1}$ (CH$_2$), 1354 cm$^{-1}$ (CH$_3$O).

NMR (CCl$_4$) (δvalue): 1.11 (3H, CH$_3$—C); 2.26–2.55 (2H, CH$_2$COO); 2.55–2.85 (2H, CH$_2$—C≡); 3.61, 3.65 (6H, CH$_3$OCO); 4.18–4.39

REFERENCE EXAMPLE 3

Methyl 4-acetyl-4-methoxycarbonyl-3-dimethoxymethyl-6-nonynoate (530 mg) is dissolved in 20 ml of tetrahydrofuran, and 25 ml of 1% aqueous solution of perchloric acid is added to the solution. The mixture is stirred at 26° to 28° C. for 12 hours. Subsequently the reaction mixture is neutralized with sodium bicarbonate and concentrated in a vacuum. The residue is extracted with ethyl acetate. The extract is dried and then concentrated to give methyl 4-acetyl-4-methoxycarbonyl-3-formyl-6-nonynoate (compound (8), R$_1$=R$_2$=CH$_3$) in a yield of 98.3%.

NMR (CCl$_4$): 9.65 (CHO).

IR: 2841 cm$^{-1}$ (CHO), 1733, 1716 cm$^{-1}$ (>C=O).

The compound (8) (500 mg) obtained above is dissolved in 200 ml of benzene containing 1 ml of acetic acid and 1 ml of piperidine, and the solution is refluxed for 6 hours. On completion of the reaction, the solvent is removed and the residue dissolved in ethyl acetate. The solution is washed with 10% hydrochloric acid and an aqueous solution of sodium bicarbonate and then dried. The product is concentrated, and the residue purified by a silica gel column, giving 5-methoxycarbonyl-4-methoxycarbonylmethyl-5-(2-pentynyl)-2-cyclopentenone (compound (2), R$_1$=R$_2$=CH$_3$) in a yield of 81%, b.p. 110°–115° C./0.15 mm Hg.

| Elementary analysis: | C | H |
| --- | --- | --- |
| Found (%) | 64.64 | 6.30 |
| Calculated (%) | 64.74 | 6.52 |

NMR (CCl$_4$): 1.05 (t, 3, CH$_3$), 1.80–2.30 (m, 2, CH$_2$C≡C), 2.34–2.86 (m, 4, CH$_2$C=C, CH$_2$CO), 3.61, 3.67 (2s, 6, CH$_3$O), 6.14 (dd, 1, 6 Hz, 2 Hz, C=CHCO), 7.59 (dd, 1, 6 Hz, 2 Hz, HC=CCO).

REFERENCE EXAMPLE 4

Methyl 4-acetyl-4-tert-butoxycarbonyl-3-dimethoxymethyl-6-nonynoate (546 mg) is dissolved in 30 ml of tetrahydrofuran, and 25 ml of 1.5% aqueous solution of perchloric acid is added to the solution. The mixture is stirred at 28° C. for 12 hours. Subsequently the reaction mixture is neutralized with sodium bicarbonate and concentrated in a vacuum. The residue is extracted with ethyl acetate. The extract is dried and then concentrated to give methyl 4-acetyl-4-tert-butoxycarbonyl-3-formyl-6-nonynoate (compound (8), R$_1$=t-Bu, R$_2$=CH$_3$) in a yield of 98.0%.

NMR (CCl$_4$): 9.65 (CHO).

IR (neat): 2841 cm$^{-1}$ (CHO), 1733, 1716 cm$^{-1}$ (>C=O),

A 790 mg quantity of the compound (8) obtained above is dissolved in 50 ml of benzene containing 1 ml of acetic acid and 1 ml of piperidine, and the solution is refluxed for 4 hours. On completion of the reaction, the solvent is removed, and the residue dissolved in ethyl acetate. The solution is washed with water and an aqueous solution of sodium bicarbonate and thereafter dried. The residue is distilled in a vacuum, giving 5-tert-butoxycarbonyl-4-methoxycarbonylmethyl-5-(2-pentynyl)-2-cyclopentenone (compound (2), R$_1$=t-Bu, R$_2$=CH$_3$) is a yield of 78%, b.p. 82°–86° C./0.006 mm Hg.

| Elementary analysis: | C | H |
| --- | --- | --- |
| Found (%) | 67.36 | 7.70 |
| Calculated (%) | 67.48 | 7.55 |

NMR (CCl$_4$): 1.02 (t 3, CH$_3$), 1.37 (bs 9, CH$_3$), 1.76–2.73 (m. 6, CH$_2$C=C, CH$_2$CO), 3.33–3.58 (m. 1, CH), 3.66 (s 3, CH$_3$O), 6.10 (dd. 1, 5 Hz, 2 Hz, C=CHCO), 7.50 (dd. 1, 5 Hz, 2 Hz, HC=CCO).

REFERENCE EXAMPLE 5

Methyl 4-acetyl-4-methoxycarbonyl-3-dimethoxymethyl-6-nonynoate (530 mg) is dissolved in 50 ml of tetrahydrofuran, and 1 ml of acetic acid and 1 ml of piperidine are added to the solution. The mixture is refluxed for 6 hours. On completion of the reaction, the solvent is removed, and the residue dissolved in ethyl acetate. The solution is washed with 10% hydrochloric acid and an aqueous solution of sodium bicarbonate, then dried and thereafter concentrated. Purification of the residue by a silica gel column affords 5-methoxycarbonyl-4-methoxycarbonylmethyl-5-(2-pentynyl)-2-cyclopentenone (compound (2), R$_1$=R$_2$=CH$_3$) in a yield of 70.5%.

REFERENCE EXAMPLE 6

Ethyl 4-acetyl-4-methoxycarbonyl-3-dimethoxymethyl-6-nonyonate (550 mg) is dissolved in 50 ml of benzene, and 1 ml of acetic acid and 1 ml of piperidine are added to the solution. The mixture is refluxed for 10 hours. On completion of the reaction, the solvent is removed, and the residue dissolved in ethyl acetate. The solution is washed with 10% hydrochloric acid and an aqueous solution of sodium bicarbonate, dried and concentrated. The residue is purified by silica gel column, giving 5-methoxycarbonyl-4-ethoxycarbonylmethyl-5-(2-pentynyl)-2-cyclopentenone (compound (2), R$_1$=CH$_3$, R$_2$=C$_2$H$_5$) in a yield of 47%.

REFERENCE EXAMPLE 7

A 800 mg quantity of 5-tert-butoxycarbonyl-4-methoxycarbonylmethyl-5-(2-pentynyl)-2-cyclopentenone is dissolved in 50 ml of benzene, and 30 mg of p-toluenesulfonic acid is added to the solution. The mixture is refluxed for 30 minutes. The resulting reaction mixture is neutralized with sodium bicarbonate, and the solvent removed. The residue is purified by a silica gel column and distilled in a vacuum, giving 4-methoxycarbonylmethyl-5-(2-pentynyl)-2-cyclopentenone (compound (3), R$_2$=CH$_3$) in a yield of 93%, b.p. 102°–103° C./3 mm Hg.

IR: 2230 cm$^{-1}$ (C≡C).

NMR (CDCl$_3$): 1.06 (t. 7, 2 Hz, 3H, CH$_3$), 1.44–3.02 (m. 12H), 3.70 (s. 3H, CH$_3$O).

EXAMPLE 1

4-Methoxycarbonylmethyl-5-(2-pentynyl)-2-cyclopentenone (890 mg) and 350 mg of sodium borohydride are dissolved in 20 ml of methanol, and the mixture is refluxed at 80° C. for one hour. On completion of the reaction, the mixture is cooled to room temperature. With addition of 60 ml of acetic acid, the mixture is stirred for 30 minutes and thereafter concentrated in a vacuum. The residue is purified with a silica gel column and distilled in a vacuum, affording 3-methoxycarbonylmethyl-2-(2-pentynyl)cyclopentanol (compound (1), $R_2=CH_3$) in a yield of 94%, b.p. 65°–69° C./0.15 mm Hg.

NMR (CCl$_4$) 0.99 (t. 3, CH$_3$), 1.22–2.88 (m. 13), 3.61 (s. 3, CH$_3$O), 2.55–2.85 (2H, CH$_2$C≡).

What is claimed is:

1. A 2-(2-pentynyl)cyclopentanol derivative represented by the formula

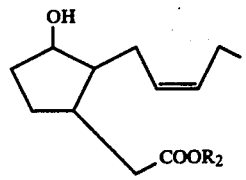

wherein $R_2$ is lower straight-chain or branched-chain alkyl, alkenyl or aralkyl.

* * * * *